US00PP15609P2

(12) United States Plant Patent

Olesen et al.

(10) Patent No.: US PP15,609 P2
(45) Date of Patent: Mar. 1, 2005

(54) ROSE PLANT NAMED 'POULCS008'

(50) Latin Name: *Rosa hybrida*
Varietal Denomination: POULcs008

(75) Inventors: L. Pernille Olesen, Fredensborg (DK); Mogens N. Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 0 days.

(21) Appl. No.: 10/738,797

(22) Filed: Dec. 16, 2003

(51) Int. Cl.[7] ..... A01H 5/00
(52) U.S. Cl. ..... Plt./146

(58) Field of Search ..... Plt./146, 141, 145, Plt./102, 105

(56) References Cited

U.S. PATENT DOCUMENTS

PP9,637 P * 9/1996 Olesen et al. ..... Plt./104

* cited by examiner

*Primary Examiner*—Anne Marie Grunberg
*Assistant Examiner*—June Hwu

(57) ABSTRACT

A new garden rose plant of the floribunda class which has abundant, yellow-apricot flowers and attractive foliage. This new and distinct variety has shown to be uniform and stable in the resulting generations from asexual propagation.

2 Drawing Sheets

Botanical classification: *Rosa hybrida.*
Variety denomination: 'POULcs008'.

SUMMARY OF THE INVENTION

The present invention constitutes a new and distinct variety of garden rose plant which originated from a controlled crossing between the female parent, an unnamed seedling, and the male pollen parent, 'POULurt' described and illustrated in U.S. Plant Pat. No. 9,637 issued Sep. 3, 1996. The two parents were crossed during the summer of 1993 and the resulting seeds were planted in a controlled environment in Fredensborg, Denmark. The new variety is named 'POULcs008'.

The new variety may be distinguished from its seed parent by the following combination of characteristics:

1. The seed parent has an orange red flower color while 'POULcs008' has a yellow orange blend flower color.
2. The seed parent has a wild rose scent whereas, 'POULcs008' has little or no scent.
3. The seed parent has an average height of 50 cm, whereas, the same of 'POULcs008' ranges from 60 to 100 cm.

The new variety may be distinguished from its pollen parent, 'POULurt' plant by the following combination of characteristics:

1. The pollen parent has a range from 15 to 25 petals whereas 'POULcs008' has a range from 25 to 30 petals.
2. The pollen parent has a small flower size 4.5 cm, while 'POULcs008' has a medium flower size between 8 cm and 10 cm.

The objective of the hybridization of this rose variety was to create a new and distinct variety for garden use with unique qualities, such as:

1. Uniform and abundant yellow-apricot flowers;
2. Vigorous, but compact growth when propagated both as a budded rose and on its own roots;
3. Disease resistance.

This combination of qualities is not present in previously available commercial cultivars of this type, known to the inventors, and distinguish 'POULcs008' from all other varieties of which we are aware.

As part of their rose development program, L. Pernille Olesen and Mogens N. Olesen germinated the seeds from the aforementioned hybridization during winter 1993 and conducted evaluations on the resulting seedlings in a controlled environment in Fredensborg, Denmark.

'POULcs008' was selected in the spring 1994 by the inventors as a single plant from the progeny of the aforementioned hybridization.

Asexual reproduction of 'POULcs008' by traditional budding and rooted cuttings was first done by L. Pernille and Mogens N. Olesen in their nursery in Fredensborg, Denmark in July, 1994. This initial and other subsequent asexual propagations conducted in controlled environments have demonstrated that the characteristics of 'POULcs008' are true to type and are transmitted from one generation to the next.

BRIEF DESCRIPTION OF THE DRAWING

The accompanying color illustration shows as true as is reasonably possible to obtain in color photographs of this type, the typical characteristics of the buds, flowers, leaves, and stems, of 'POULcs008'. Specifically illustrated in SHEET 1:

FIG. 1.1; Stem showing open flower, branching, and the attachment of leaves, buds, and peduncles;

FIG. 1.2; Flower bud closed, flower bud as sepals unfold, and partially open flower;

FIG. 1.3; Flower petals, detached;

Specifically illustrated in SHEET 2:

FIG. 2.1; Sepals, receptacle, and peduncle;

FIG. 2.2; Bare stem exhibiting thorns.

FIG. 2.3; Mature leaves and juvenile leaves;

DETAILED DESCRIPTION OF THE VARIETY

The following is a description of 'POULcs008', as observed in its growth in a field nursery in Jackson County, Oreg. Observed plants are 3 years of age. Color references are made using The Royal Horticultural Society (London, England) Colour Chart, 1995, except where common terms of color are used.

For a comparison, several physical characteristics of the rose variety 'POULcs003', a rose variety from the same inventors described and illustrated in U.S. Plant patent application Ser. No. 10/342,697 dated Jan. 14, 2003, are compared to 'POULcs008' in Chart 1.

CHART 1

| | 'POULcs008' | 'POULcs003' |
|---|---|---|
| Petal count | 25 to 30 petals. | 20 to 40 petals. |
| General tonality | Yellow-Orange Group 19B. | Orange Group 24D. |
| Flower diameter | 65 mm. | 70 to 80 mm. |

FLOWER AND FLOWER BUD

Blooming habit: Continuous.

Flower bud:

*Size.*—Upon opening, 40 mm in length from base of receptacle to end of bud. Bud diameter is 10 to 12 mm.

*Bud form.*—Long, pointed ovoid.

*Bud color.*—As sepals unfold, petals are Yellow Group 7A at the basal zone. Flower color gradually transitions at the marginal zone to Yellow-Orange Group 22B with intonations of Yellow-Orange Group 21B.

*Sepals.*—Upper Surface: Color: Green Group 138B. Texture: Smooth and pubescent. Lower Surface: Color: Yellow-Green Group 144A. Shape: Sepal apex is cirrhose. Base is flat at union with receptacle. Margins: Weak foliaceous appendages on three of the five sepals. Size: 35 mm (l)×7 mm (w).

*Receptacle.*—Surface: Smooth. Shape: Urn-shaped. Size: 5 mm (h)×6 mm (w). Color: Yellow-Green Group 144A.

*Peduncle.*—Surface: Smooth. Slightly pubescent. Length: 30 to 35 mm average length. Diameter: 3 mm. Color: Yellow-Green Group 144A. Strength: Somewhat to strong.

*Borne.*—Multiples of 12 flower buds per stem.

Flower bloom:

*Fragrance.*—Light earthy rose scent.

*Duration.*—The blooms have a duration on the plant of approximately 10 to 12 days. Afterwards, petals fall cleanly away from plant.

*Size.*—Average flower diameter is 65 mm when fully open.

*Form.*—General shape is an open cup with petals that curve out from the center. Petals overlap somewhat.

*Shape of flower when viewed from the side.*—Upon opening, upper part: Flat. Upon opening, lower part: Flattened convex. Open flower, upper part: Flattened convex. Open flower, lower part: Flattened convex.

*Petalage.*—On average the petal count ranges from 28 to 33 petals under normal conditions with 3 petaloids.

*Color.*—Upon opening, petals: Outermost petals: Outer side: At basal zone, Yellow Group 7A. Color transitions gradually at the middle zone to Yellow-Orange Group 22B with intonations of Yellow-Orange Group 21B. Inner Side: Yellow Group 9B at base blending with Yellow-Orange Group 20B at the middle zone. Innermost petals: Outer side: At the basal zone Yellow-Orange Group 15C. Blending with Orange Group 24B to become fully Orange Group 24 B at marginal zone. Inner Side: Predominantly Yellow-Orange Group 15C with intonations of Yellow-Orange Group 21C. Upon opening, basal petal spots: Outermost petals: Outer side: Yellow Group 9C. Inner Side: Yellow Group 9B. Innermost petals: Outer side: Yellow Group 9C. Inner Side: Yellow Group 9B. After opening, petals: Outermost petals: Outer side: At the basal zone, Yellow Group 9C. Blending with Yellow-Orange Group 20C at middle zone. Inner Side: Basal Yellow Group 9C. Blending with Yellow-Orange Group 18B at middle zone. Innermost petals: Outer side: At the basal zone, Yellow Group 9C. Blending with Yellow-Orange Group 20C at middle zone. Inner Side: Basal Yellow Group 9C. Blending with Yellow-Orange Group 18B at middle zone. After opening, basal petal spots: Outermost petals: Outer Side: Yellow Group 9C. Inner Side: Yellow Group 9B. Innermost petals: Outer Side: Yellow Group 9C. Inner Side: Yellow Group 9B.

General tonality: On open flower, Yellow-Orange Group 19B. No change in the general tonality at the end of the 10th day.

*Petals.*—Petal Reflex: Petals reflex slightly. Margin: Entire with occasional cleft and point in center of margin. Shape: Apex: Round. Base: Acute. Size: 35 to 40 mm length by 30 to 35 mm in width. Texture: Smooth. Thickness: Thin. Arrangement: Not Formal.

*Petaloids.*—Quantity: 2 to 3. Color: Upper Surface: Yellow-Orange Group 21C. Lower Surface: Yellow-Orange Group 15C. Size: 30 mm in length by 20 to 25 mm wide.

Reproductive organs:

*Pistils.*—Length: 8 mm. Quantity: 60.

*Pollen.*—None observed.

*Anthers.*—Length: 3 mm. Color: Yellow-Orange Group 22A. Quantity: 80 actual count.

*Filaments.*—Color: Yellow-Orange Group 14A. Length: 9 to 11 mm.

*Stigmas.*—Slightly inferior in height relative to the anthers. Color: Yellow Group 12A.

*Styles.*—Color: Yellow Group 4D. Other Intonations: Greyed-Red Group 180C. Texture: Slightly pubescent.

*Hips.*—None Observed in the field nursery in Jackson County Oreg.

PLANT

Plant growth: Moderate, upright to bushy. When grown as a budded field grown plant on *Rosa multiflora* understock, the average height of the plant is 100 cm and the average width is 100 cm.

Stems:

*Color.*—Young wood: Yellow-Green Group 144B. Older wood: Yellow-Green Group 144A.

*Surface texture.*—Young wood: Smooth. Older wood: Smooth.

*Thorns.*—Incidence: 17 thorns per 10 cm of stem. Size: Average length: 5 mm. Color: Juvenile thorns are Greyed-Red Group 181A. Mature thorns are Greyed-Yellow Group 160B. Shape: Linear to slightly concave.

Plant foliage: Normal number of leaflets on leaves in middle of the stem: 7 leaflets.

*Compound leaf size.*—140 to 150 mm in length by 90 to 100 mm wide.

*Quantity.*—Above average.

*Color.*—Mature Foliage: Upper surface is Yellow-Green Group 139A to 141A. Lower surface is Yellow-Green Group 146A. Juvenile foliage: Upper surface is Yellow-Green Group 139A to 141A. Lower surface is Yellow-Green Group 146A.

*Plant leaves and leaflets.*—Stipules: Size: 20 mm. Color: Yellow-Green Group 144A. Margins: Many stipitate glands. Petiole: Length: 30 mm. Color: Yellow-Green Group 144A. Underneath: Bi-colored prickles Greyed-Yellow Group 160B at base. Apex is Greyed-Red Group 178B. Margins: Stipitate glands along margin. Rachis: Color: Yellow-Green Group 144A. Size: 55 mm. Underneath: Bi-colored prickles Greyed-Yellow Group 160B at base. Apex is Greyed-Red Group 178B. Margins: Stipitate glands along margin. Leaflet: Size: 40 mm (l)×30 mm (w). Edge: Serrated. Shape: Broadly ovate. Leaf apex is cuspidate. Leaf base is rounded. Texture: Smooth. Arrangement: Odd pinnate. Venation: Reticulate. Glossiness: Very glossy.

Disease resistance: Above average resistance to mildew, rust, black spot, and Botrytis under normal growing conditions in Jackson County, Oreg.

Cold hardiness: The variety 'POULcs008' has been found to be cold tolerant to USDA Cold Hardiness Zone 6.

It is claimed:

1. A new and distinct variety of rose plant of the floribunda rose class, substantially as herein illustrated and described as a distinct and novel rose variety due to its abundant yellow-apricot, disease resistance, and extended period of bloom.

* * * * *

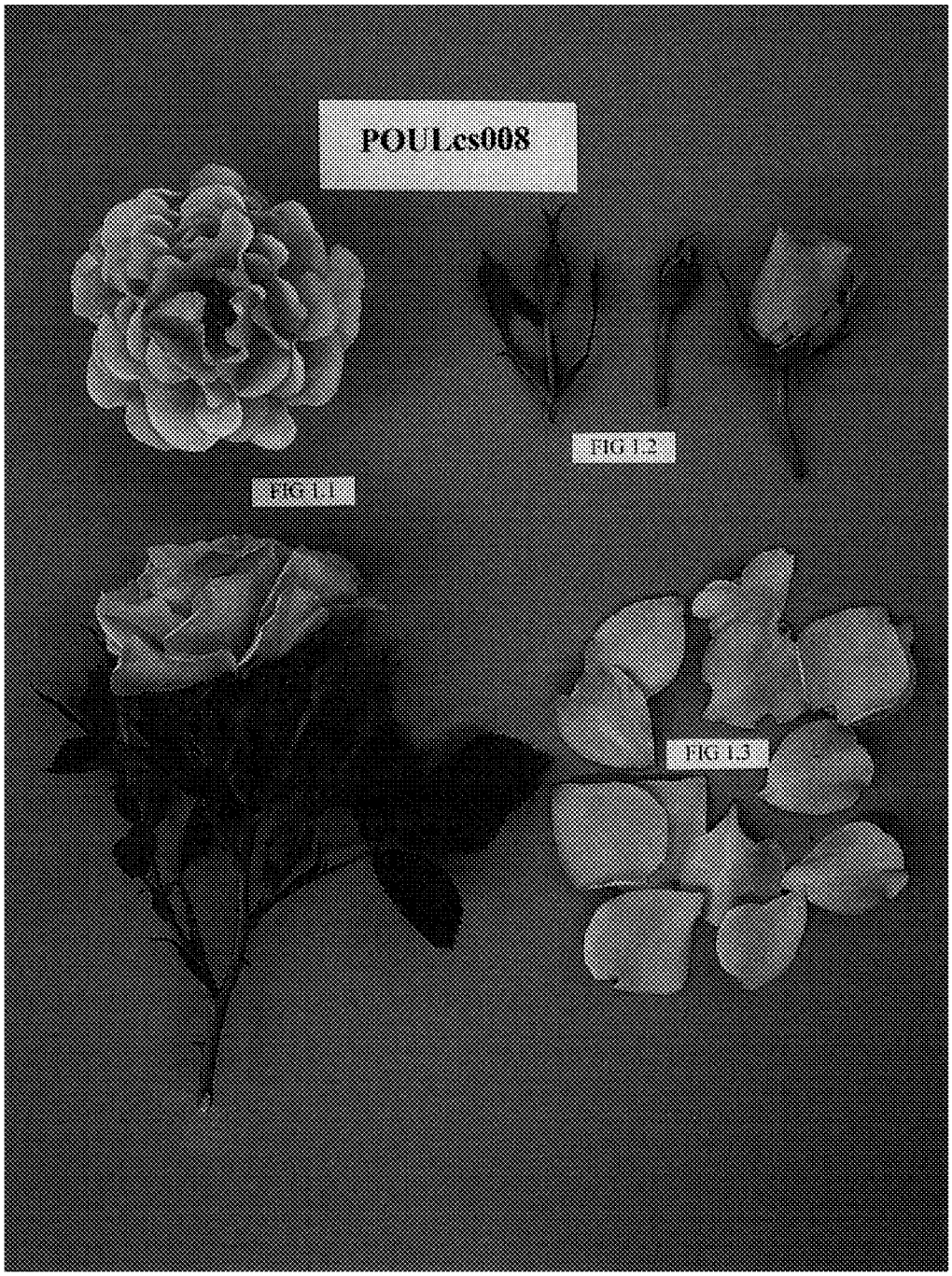
POULcs008
FIG 1.1
FIG 1.2
FIG 1.3

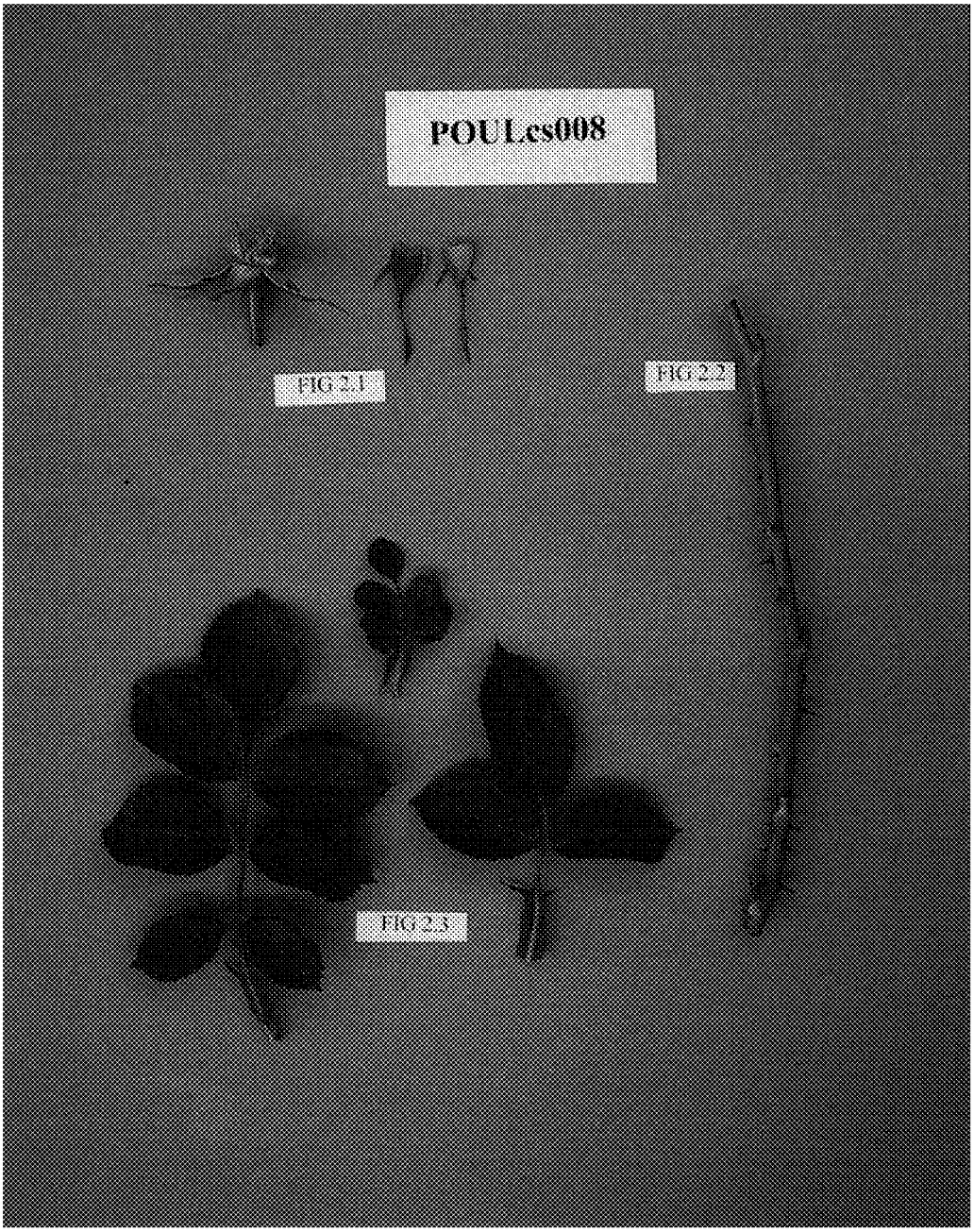
POULcs008
FIG 2.1
FIG 2.2
FIG 2.3